(12) United States Patent
Sliwa et al.

(10) Patent No.: US 9,108,037 B2
(45) Date of Patent: Aug. 18, 2015

(54) APPARATUS AND METHOD FOR TISSUE ABLATION WITH NEAR-FIELD COOLING

(75) Inventors: John W. Sliwa, Los Altos Hills, CA (US); Stephen A. Morse, Menlo Park, CA (US); John P. Goetz, Aptos, CA (US)

(73) Assignee: St. Jude Medical, Atrial Fibrillation Division, Inc., St. Paul, MN (US)

( * ) Notice: Subject to any disclaimer, the term of this patent is extended or adjusted under 35 U.S.C. 154(b) by 1360 days.

(21) Appl. No.: 12/400,198

(22) Filed: Mar. 9, 2009

(65) Prior Publication Data

US 2010/0228162 A1    Sep. 9, 2010

(51) Int. Cl.
*A61B 18/04* (2006.01)
*A61N 7/02* (2006.01)
*A61B 17/225* (2006.01)
*A61B 17/00* (2006.01)
*A61B 18/00* (2006.01)

(52) U.S. Cl.
CPC ............... *A61N 7/02* (2013.01); *A61B 17/2251* (2013.01); *A61B 2017/00084* (2013.01); *A61B 2018/00011* (2013.01)

(58) Field of Classification Search
USPC .......................................... 606/27, 28, 34, 41
See application file for complete search history.

(56) References Cited

U.S. PATENT DOCUMENTS

| | | | | |
|---|---|---|---|---|
| 5,301,687 A | * | 4/1994 | Wong et al. | ............ 607/116 |
| 5,348,554 A | | 9/1994 | Imran et al. | |
| 5,415,654 A | * | 5/1995 | Daikuzono | .............. 606/15 |
| 5,423,811 A | | 6/1995 | Imran et al. | |
| 5,529,067 A | * | 6/1996 | Larsen et al. | ............ 600/374 |
| 5,545,161 A | | 8/1996 | Imran | |
| 5,688,267 A | * | 11/1997 | Panescu et al. | ............ 606/41 |
| 5,697,927 A | | 12/1997 | Imran et al. | |
| 5,762,066 A | * | 6/1998 | Law et al. | ............ 600/439 |
| 5,792,140 A | | 8/1998 | Tu et al. | |
| 5,843,152 A | | 12/1998 | Tu et al. | |
| 5,893,884 A | | 4/1999 | Tu | |
| 5,913,856 A | | 6/1999 | Chia et al. | |
| 5,935,124 A | | 8/1999 | Klumb et al. | |

(Continued)

OTHER PUBLICATIONS

D'Avila et al., "Temporary Occlusion of the Great Cardiac Vein and Coronary Sinus to Facilitate Radiofrequency Catheter Ablation of the Mitral Isthmus," 19(6) J. Cardiovascular Electrophysiol. 645-650 (Jun. 2008).

(Continued)

*Primary Examiner* — Michael Peffley
*Assistant Examiner* — Daniel Fowler
(74) *Attorney, Agent, or Firm* — Wiley Rein LLP

(57) ABSTRACT

A tissue ablation system facilitates lesioning deep tissue while preventing damage to superficial tissue and includes a probe having a distal end portion, at least one transducer carried on the distal end portion, and at least one acoustically transparent heat removal element thermally coupled to a target tissue within the beam path of the transducer. The transducer delivers acoustic energy to the tissue through the heat removal element in order to ablate the tissue; the heat removal element removes sufficient thermal energy from the tissue volume to prevent thermal necrosis in superficial tissue. The heat removal element may be a heat sink or a convective element. An optional temperature sensor provides advisory data to a practitioner and/or is coupled to a feedback control system operable to control delivery of acoustic energy to the tissue and/or a rate of thermal energy removal therefrom.

18 Claims, 3 Drawing Sheets

(56) References Cited

U.S. PATENT DOCUMENTS

| | | | |
|---|---|---|---|
| 5,938,659 A | 8/1999 | Tu et al. | |
| 6,217,576 B1 | 4/2001 | Tu et al. | |
| 6,383,180 B1* | 5/2002 | Lalonde et al. | 606/22 |
| 6,419,648 B1* | 7/2002 | Vitek et al. | 601/3 |
| 6,500,174 B1* | 12/2002 | Maguire et al. | 606/41 |
| 6,575,969 B1* | 6/2003 | Rittman et al. | 606/41 |
| 6,618,620 B1* | 9/2003 | Freundlich et al. | 607/27 |
| 6,635,054 B2* | 10/2003 | Fjield et al. | 606/27 |
| 6,641,579 B1* | 11/2003 | Bernardi et al. | 606/27 |
| 6,645,202 B1* | 11/2003 | Pless et al. | 606/41 |
| 6,689,128 B2 | 2/2004 | Sliwa et al. | |
| 6,701,931 B2 | 3/2004 | Sliwa et al. | |
| 6,858,026 B2 | 2/2005 | Sliwa et al. | |
| 6,942,661 B2 | 9/2005 | Swanson | |
| 2003/0014046 A1* | 1/2003 | Edwards et al. | 606/41 |
| 2004/0049251 A1* | 3/2004 | Knowlton | 607/101 |
| 2004/0267167 A1* | 12/2004 | Podany et al. | 601/2 |
| 2006/0025756 A1* | 2/2006 | Francischelli et al. | 606/27 |
| 2006/0052778 A1* | 3/2006 | Chapman et al. | 606/51 |
| 2006/0058711 A1* | 3/2006 | Harhen et al. | 601/2 |
| 2006/0069343 A1* | 3/2006 | Rontal | 604/20 |
| 2006/0074314 A1* | 4/2006 | Slayton et al. | 600/439 |
| 2007/0299435 A1 | 12/2007 | Crowe et al. | |
| 2008/0114342 A1* | 5/2008 | Whayne et al. | 606/15 |
| 2008/0195003 A1* | 8/2008 | Sliwa et al. | 601/3 |

OTHER PUBLICATIONS

D' Avila, A. and Dukkipati, S., "Esophageal Damage during Catheter Ablation of Atrial Fibrillation: Is Cryo Safer than RF?" 32(6) Pacing Clinic. Electrophysiol. 709-710 (Jun. 2009).

* cited by examiner

APPARATUS AND METHOD FOR TISSUE ABLATION WITH NEAR-FIELD COOLING

BACKGROUND OF THE INVENTION a. Field of the Invention

The instant invention generally relates to devices and methods for treating electrophysiological diseases of the heart. In particular, the instant invention relates to devices and methods for ablation for the treatment of atrial fibrillation.

b. Background Art

It is well known that atrial fibrillation results from disorganized electrical activity in the heart muscle (the myocardium). The surgical maze procedure has been developed for treating atrial fibrillation, and involves the creation of a series of surgical incisions through the atrial myocardium in a preselected pattern so as to create conductive corridors of viable tissue bounded by scar tissue.

As an alternative to the surgical incisions of the maze procedure, transmural ablations of the heart may be used. Such ablations may be performed either from within the chambers of the heart (endocardial ablation), using endovascular devices (e.g., catheters) introduced through arteries or veins, or from outside the heart (epicardial ablation) using devices introduced into the patient's chest via thoracic incisions (e.g., thoracotomies). Various ablation techniques may be used, including, but not limited to, cryogenic ablation, radio frequency (RF) ablation, laser ablation, ultrasonic ablation, and microwave ablation. The ablation devices are used to create elongated transmural lesions—that is, extended blocking lesions passing through a sufficient thickness of the myocardium to block electrical conduction—forming the boundaries of the conductive corridors in the atrial myocardium. Perhaps most advantageous about the use of transmural ablation rather than surgical incision is the ability to perform ablation procedures without first establishing cardiopulmonary bypass (CPB).

A transmural lesion need not, however, extend all the way to the surface of the tissue being treated. This is particularly true for ventricular burns and ventricular rhythm disorders. Often, there are structures, such as coronary arteries, near the surface of the ventricular tissue, that are to be protected from thermal damage and/or thermal necrosis when creating transmural lesions in deeper tissue. With certain ablation techniques, such as RF ablation and cryogenic ablation, it is difficult to create effective sub-surface lesions without also causing thermal damage and/or thermal necrosis in this more superficial tissue. Indeed, many ablation techniques cannot effectively be used to deliver sufficient ablative energy to create an effective lesion in deeper tissue without also delivering sufficient energy to thermally damage more superficial tissue.

BRIEF SUMMARY OF THE INVENTION

It is therefore an object of the present invention to provide a tissue ablation device capable of forming effective lesions in sub-surface tissue without causing thermal damage and/or thermal necrosis in more superficial tissue.

Another object of the present invention is to provide a tissue ablation device that can deliver sufficient amounts of ablative energy to deeper tissue without heating more superficial tissue to the point of thermal damage and/or thermal necrosis.

Still another object of the present invention is to provide a method of ablating tissue that creates effective transmural lesions below a certain depth in the tissue while preventing the creation of lesions above that depth in the tissue.

Disclosed herein is a tissue ablation system that includes: a probe having a distal end portion; at least one transducer carried on the distal end portion of the probe and capable of emitting acoustic energy along a beam path; and at least one acoustically transparent heat removal element adapted to be thermally coupled to a tissue volume within the beam path of the at least one transducer in order to remove sufficient thermal energy from the tissue volume to prevent thermal necrosis to a preset depth in the tissue volume. In some aspects, the at least one acoustically transparent heat removal element is carried on the distal end portion of the probe and is thermally coupled to the at least one transducer to remove thermal energy from the at least one transducer in addition to removing thermal energy from the tissue volume. It is also contemplated that the at least one acoustically transparent heat removal element includes a fluid-receiving chamber at least partially enclosed by a flexible membrane, such that the flexible membrane permits the at least one transducer to be conformably acoustically coupled to the tissue volume.

The at least one acoustically transparent heat removal element may be at least one heat sink (that is, an element that operates in conduction and/or radiation) or at least one convective heat removal element. In some embodiments, the at least one convective heat removal element is in the shape of an annular ring, and a cooling fluid may flow through a central passageway of the ring. It is also desirable for the thickness of the at least one cooling element to be less than the maximum lateral direction thereof. This provides a relatively short acoustic pathway between the transducer and the tissue without disadvantageously reducing the contact surface area between the heat removal element and the tissue.

When a convective heat removal element is utilized, it may be part of a closed-loop flowed cooling system or an open-loop flowed cooling system. Optionally, in an open-loop flowed cooling system, the at least one convective heat removal element may include at least one fluid outlet through which a cooling fluid may be discharged in vivo, typically in a direction substantially parallel to a surface of the tissue volume being treated and cooled, which both increases the cooling effect and facilitates wetted acoustic coupling to the tissue.

Optionally, the system includes at least one temperature sensor positioned to sense a temperature of one or more of the at least one transducer, the at least one acoustically transparent heat removal element, a cooling fluid flowing through the at least one acoustically transparent heat removal element, and the tissue volume to which the at least one heat removal element is coupled. The at least one temperature sensor may provide advisory data to a practitioner and/or may be coupled to a feedback control system operable to control at least one of a rate at which the at least one transducer delivers energy to the tissue volume and a rate at which the at least one heat removal element removes thermal energy from the tissue volume in order to prevent thermal necrosis to the preset depth in the tissue volume. To this end, it is contemplated that the system may include a controller coupled to the at least one transducer and/or the at least one heat removal element that is programmed to control a rate at which the at least one transducer delivers acoustic energy into the tissue volume and/or a rate at which the at least one acoustically transparent heat removal element removes thermal energy from the tissue volume.

To determine the preset depth within which prevention of thermal necrosis is desirable, the system may include at least one coronary artery detection element carried on the distal end portion of the probe. Suitable coronary artery detection elements include, but are not limited to, infrared detectors, microphones, acoustic Doppler sensors (such as the transducer itself when operated in Doppler mode), and pulsatility sensors. The probe may also optionally include one or more electrodes suitable for electrophysiological studies, pacing, sensing, localization, and the like.

Also disclosed herein is a method of ablating tissue that includes the following steps: acoustically coupling at least one transducer capable of emitting acoustic energy along a beam path to a tissue to be treated; thermally coupling at least one acoustically transparent heat removal element to the tissue to be treated within the beam path of the at least one transducer; activating the at least one transducer to emit acoustic energy through at least a portion of the at least one acoustically transparent heat removal element and into the tissue to be treated; and removing sufficient thermal energy from the tissue to be treated via the at least one acoustically transparent heat removal element to prevent thermal necrosis to a preset depth in the tissue while simultaneously delivering sufficient acoustic energy into the tissue to be treated to cause thermal necrosis beyond the preset depth. It is contemplated that the at least one transducer may be acoustically coupled to the tissue to be treated using the at least one acoustically transparent heat removal element.

In certain aspects, the method also includes monitoring a temperature of at least one of the at least one transducer, the at least one acoustically transparent heat removal element, a cooling fluid flowing through the at least one acoustically transparent heat removal element, and the tissue to be treated. In response to the monitored temperature, a rate at which the at least one acoustically transparent heat removal element removes thermal energy from the tissue to be treated may be adjusted (either automatically via a suitable controller or manually by a practitioner) in order to prevent thermal necrosis to the preset depth in the tissue.

Prior to or during the delivery of energy to the tissue, the method may also include detecting one or more structures within the tissue to be treated that are to be protected from thermal necrosis. The preset depth may then be set, adjusted, or readjusted to a level below the one or more detected structures in order to protect the one or more detected structures from thermal necrosis. Optionally, at least one of lesion formation in the tissue to be treated and a thickness of the tissue to be treated may be monitored via pulse-echo feedback using the at least one transducer.

In certain aspects, the steps of activating the at least one transducer and removing thermal energy from the tissue to be treated via the at least one acoustically transparent heat removal element occur in a time-interleaved manner. That is, in certain aspects, the at least one transducer and the at least one heat removal element are activated in turn or in sequence. In other aspects, the steps of activating the at least one transducer and removing thermal energy from the tissue to be treated via the at least one acoustically transparent heat removal element occur simultaneously (e.g., the at least one transducer and the at least one heat removal element operate together).

It is desirable to determine a relationship between a power level of the at least one transducer and a cooling rate of the at least one acoustically transparent heat removal element that prevents thermal necrosis of superficial tissue above the preset depth. This relationship may then be used to control the delivery of acoustic energy to the tissue to be treated and/or the removal of thermal energy from the tissue to be treated. The control may be to maintain the preset depth or, alternatively, to adjust the depth above which thermal necrosis is prevented.

In another aspect, the present invention provides a method of ablating tissue that includes the following steps: providing a probe having a distal end portion, the distal end portion including at least one transducer capable of emitting acoustic energy along a beam path and at least one convective heat removal element capable of removing thermal energy from an object thermally coupled thereto; acoustically coupling the at least one transducer to a tissue to be treated via a fluid medium flowable or flowing through the at least one convective heat removal element, the tissue having a tissue surface and a depth below the tissue surface within which thermal necrosis is to be prevented; activating the at least one transducer to deliver acoustic energy into the tissue to be treated through the at least one convective heat removal element; and flowing the fluid medium through the at least one convective heat removal element to remove thermal energy from the tissue to be treated. Within the depth below the tissue surface within which thermal necrosis is to be prevented, convective cooling effects of the fluid medium flowing through the at least one convective heat removal element are sufficient to prevent thermal necrosis. Beyond the depth below the tissue surface within which thermal necrosis is to be prevented, sufficient acoustic energy is delivered to overcome the surface cooling and cause thermal necrosis. That is, thermal necrosis is prevented in superficial tissue and permitted in deeper tissue.

An advantage of the present invention is that it provides apparatus and methods for delivering sufficient ablative energy to sub-surface tissue to create effective lesions therein without heating more superficial tissue to the point of thermal damage and/or thermal necrosis.

While, in some aspects of the present invention, the resulting subsurface lesion will be otherwise transmural (that is, reaching all the way to the far tissue wall), in other aspects of the invention, such as in certain ventricular cases, the subsurface lesion may be arranged to burn only problematic midrange tissues and not extend all the way to the far tissue wall. Advantageously, the present invention allows any desired subsurface burning configuration without thermally ablating the near surface and more superficial tissues.

The foregoing and other aspects, features, details, utilities, and advantages of the present invention will be apparent from reading the following description and claims, and from reviewing the accompanying drawings.

DETAILED DESCRIPTION OF THE INVENTION

The present invention provides a tissue ablation system useful, for example, in the treatment of atrial fibrillation or ventricular rhythm disorders. Though the present invention will be described in connection with an epicardial tissue ablation system utilizing high intensity focused ultrasound (HIFU) transducers, it is contemplated that the described features may be incorporated into any number of catheters or other devices, as would be appreciated by one of ordinary skill in the art by virtue of the teachings herein.

Figure 1:
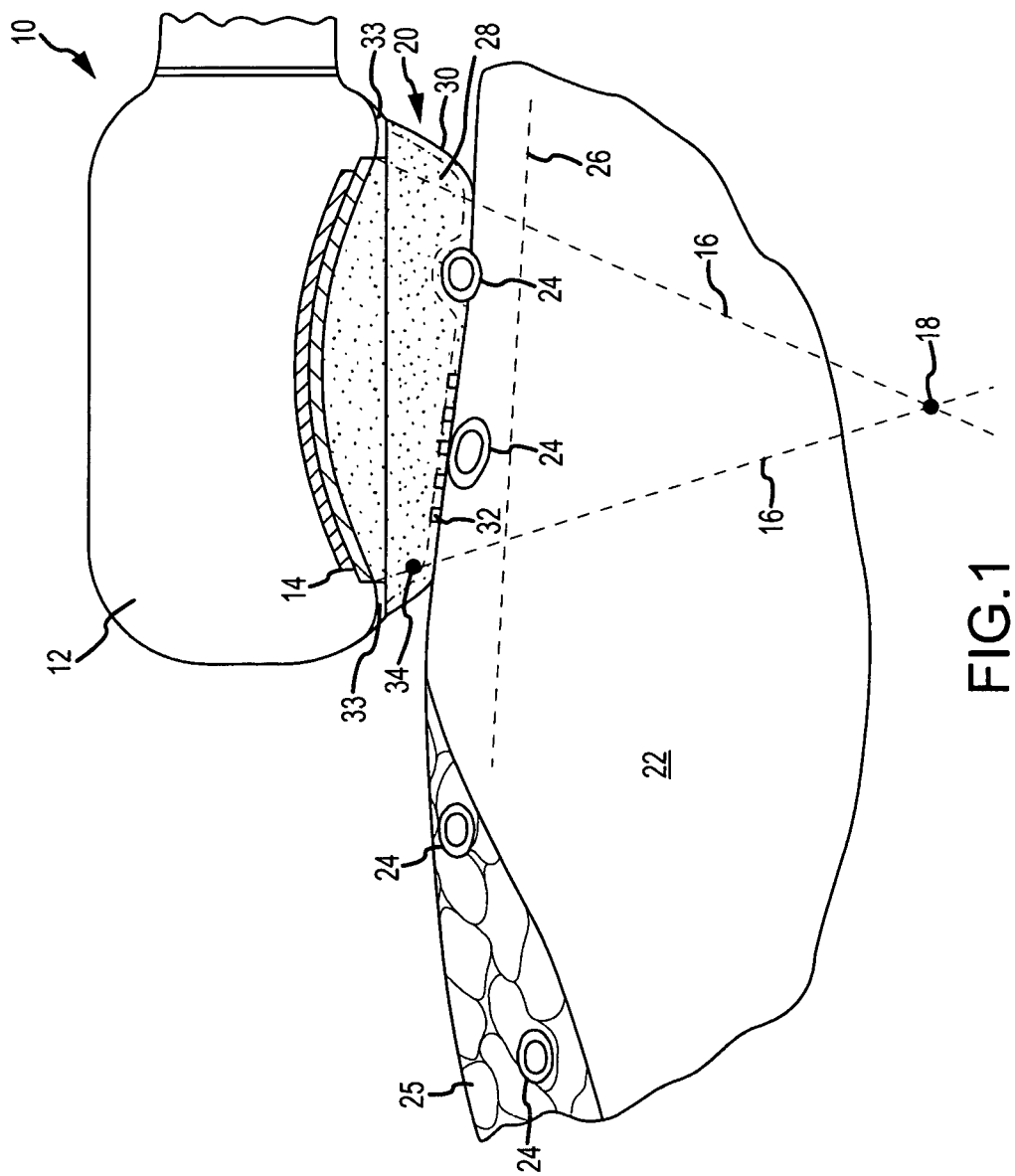
FIG. 1 depicts a tissue ablation system according to one embodiment of the present invention.

FIG. 1 depicts a tissue ablation system 10 according to a first embodiment of the present invention. Tissue ablation system 10 includes a probe, the distal end portion 12 of which is shown in FIG. 1. As used herein, the term "probe" refers to any device suitable for introducing a diagnostic or therapeutic medical device, such as the ablating transducer discussed in further detail below, into a patient's body. Thus, the term "probe" encompasses catheters, scopes, introducers, sheaths, and the like, regardless of whether controlled manually or via a robotic control system. Suitable probes include, but are not limited to, the structures disclosed in U.S. patent application Ser. No. 11/646,526, including the related patents and patent applications incorporated by reference therein, the entire disclosures of which are hereby incorporated by reference as though fully set forth herein. As will be familiar to the ordinarily skilled artisan, the proximal end portion (not shown) of the probe may include a handle, steering mechanism actuators, electrical and power connections, fluid connections, and the like as appropriate for a particular application of the probe.

Distal end portion 12 carries at least one ablation element, such as a transducer 14. According to some aspects of the invention, transducer 14 is an ultrasonic transducer, such as a high intensity focused ultrasound (HIFU) transducer. Ultrasonic transducers are well suited for use in the present invention because they facilitate creation of ablation lesions beginning at the far surface of the tissue and moving towards the near surface of the tissue (that is, starting in deep tissue and moving during formation towards more superficial tissue). One suitable algorithm for creating such a lesion is disclosed in U.S. patent application Ser. No. 11/646,526.

The ordinary artisan will appreciate that transducer 14 may take many forms. For example, transducer 14 may be a piezoelectric transducer, a magnetostrictive transducer, an electrostatic transducer, a microelectromechanical (MEMS) transducer, a capacitive MEMS ultrasonic transducer (CMUT), or any other transducer capable of emitting acoustic energy along a beam path 16 (or along another useful direction). Moreover, the ordinary artisan will understand that transducer 14 may emit acoustic energy that is focused (whether by shaping the transducer or via an acoustic lens) or that is collimated/unfocused. In FIG. 1, the acoustic energy emitted by transducer 14 is spherically focused to a focal point 18, but other arrangements (e.g., cylindrical focusing) are regarded as within the spirit and scope of the invention.

Within beam path 16 of transducer 14 is at least one heat removal element 20. Heat removal element 20 will typically be acoustically transparent so as not to effect the acoustic energy propagating therethrough. Heat removal element 20 is depicted as thermally coupled to tissue volume 22 in order to remove thermal energy therefrom. One of ordinary skill in the art will also recognize that, in the embodiment of the invention depicted in FIG. 1, heat removal element 20 also acoustically couples transducer 14 to tissue volume 22. In some aspects of the invention, the thickness (e.g., the maximum thickness, average thickness, or constant thickness) of heat removal element 20 is less than the maximum lateral dimension (e.g., the diameter, major axis, or major side) thereof. This allows acoustic energy to pass "downwards" through heat removal element 20 into tissue volume 22 along a relatively short acoustic pathway while providing a large contact surface area for tissue heat to pass "upwards" from tissue volume 22 into heat removal element 20. It should be understood that the heat passing from tissue volume 22 into heat removal element 20 includes both heat generated by the passing acoustic energy and some natural metabolic heat. Of course, it is also contemplated that multiple heat removal elements could be used in connection with each transducer (e.g., "undersized" heat removal elements). Likewise, it is contemplated that a single heat removal element could be used for multiple transducers (e.g., "oversized" heat removal elements).

Within tissue volume 22 are structures, such as coronary arteries 24, that are desirably protected from thermal necrosis. As used herein, the term "thermal necrosis" refers to any undesirable thermal damage to tissue, including, but not limited to, burning, lesioning, charring, and popping. Tissue volume 22 may also include fat 25 that may also be desirably protected from thermal necrosis (e.g., to avoid boiling superficial fat when lesioning tissue beneath the fat, which could interfere with the passage of acoustic energy). Accordingly, heat removal element 20 desirably removes sufficient thermal energy from tissue volume 22 via one or more modes of heat transfer in order to prevent thermal necrosis within a superficial, near-surface layer or preset depth (represented in FIG. 1 by the tissue above dashed line 26) therein. In other words, above dashed line 26, the cooling effects of heat removal element 20 neutralize or reverse the heating effects of the acoustic energy delivered by transducer 14. In some aspects of the invention, the heating effects of the acoustic energy delivered by transducer 14 are counteracted by precooling the superficial portion of tissue volume 22 to a temperature below 37 degrees C. This desirably precools the superficial tissues, including coronary arteries 24, to provide additional peak temperature safety margin during a subsequent ablation of underlying tissue. As used herein, the term "precooling" refers to extracting heat from tissue volume 22 before transducer 14 is activated.

Advantageously, for a focused transducer, because the intensity of the acoustic energy emitted by transducer 14 is reduced near the surface of tissue volume 22 relative to the intensity closer to focus 18, a moderate amount of cooling can achieve this result. Beyond (that is, beneath) dashed line 26, on the other hand, the cooling effects of heat removal element 20 are insufficient to neutralize or reverse the heating effects of the acoustic energy delivered by transducer 14, facilitating the creation of effective transmural lesions within the deeper reaches of tissue volume 22. As discussed in greater detail below, the ordinary artisan will recognize from this disclosure that the line 26 defining the protected preset depth can be pushed deeper into tissue volume 22, for example by reducing ablation power and/or increasing the cooling rate. Likewise, line 26 can be moved nearer to the surface of tissue volume 22, for example by increasing ablation power and/or decreasing the cooling rate. Indeed, line 26 can be moved all the way to the surface of tissue volume 22, for example by deactivating heat removal element 20.

In some embodiments of the invention, heat removal element 20 is carried on distal end portion 12 of the probe along with transducer 14. For example, as shown in FIG. 1, heat removal element 20 includes a fluid-receiving chamber 28 enclosed by a flexible membrane 30. Fluid-receiving chamber 28 stands transducer 14 off from the surface of tissue volume 22, while flexible membrane 30 allows transducer 14 to remain conformably acoustically coupled to tissue volume 22 during relative movement between the probe and tissue volume 22 (due, for example, to the beating of the heart or movement/respiration of the patient). Alternatively or additionally, a vacuum clamp may be provided to securely hold the probe onto the surface of tissue volume 22 in order to maintain the desired acoustic and thermal couplings.

In one aspect, heat removal element 20 is a convective heat removal element. As used herein, the term "convective heat removal element" refers to an element that utilizes a flowing cooling fluid to effect convective heat transfer in a mode sometimes referred to as "forced convection" or "heat advection." Any suitable cooling fluid, such as water, saline, refrigerant, or the like, may be employed, and either laminar or turbulent flow may predominate. Thus, for example, cool saline may be flowed through chamber 28, typically in a net direction substantially parallel to the surface of tissue volume 22, though some circulation within chamber 28 before being exhausted therefrom is contemplated. This both acoustically couples transducer 14 to tissue volume 22 and convectively cools tissue volume 22. The ordinary artisan will also recognize that the cooling fluid flowing through chamber 28 can remove shed heat from transducer 14 while also providing convective cooling counteracting other sources of heat into tissue volume 22 (e.g., natural body heat, including the heat of blood flowing in coronary arteries 24). Thus, coolant flow into distal end portion 12 of the probe serves both to cool transducer 14 and tissue volume 22.

Typically, the present invention utilizes either refrigerated saline or room temperature saline as the cooling fluid. In either case, the cooling fluid is cooler than the tissue being treated, and sufficiently cool so as to receive heat transfer from tissue volume 22 as it passes through heat removal element 20.

The cooling system of which such a convective heat removal element is a part may be either closed loop (that is, the cooling fluid is continually recycled) or open loop (that is, at least some of the cooling fluid is not recycled). Where the cooling system is an open loop, the loop may include one or more fluid outlets 32 (e.g., weep holes in membrane 30, which may be formed with a laser, mechanically, or by any other suitable method) through which some of the cooling fluid may be discharged in vivo. It should be understood, however, that the fluid outlets 32 serve to assure wetted acoustic coupling of transducer 14 to tissue volume 22; cooling of tissue volume 22 is primarily attributable to the convective effects of the cooling fluid flowing through chamber 28. A significant convective fluid flow through heat removal element 20 may be facilitated by providing one or more larger coolant exhaust ports 33 such that the cooling fluid exits mainly through exhaust ports 33 and only exits weep holes 32 to a lesser degree. Exhaust ports 33 typically vent the cooling fluid sideways outward along the surface of tissue volume 22. It is also contemplated that at least a portion of the cooling fluid discharged in vivo may be aspirated.

Some embodiments of the invention also include one or more temperature sensors 34, such as thermistors or thermocouples, carried by distal end portion 12 of the probe. Temperature sensor 34 may be positioned to measure the temperature of one or more of transducer 14, heat removal element 20, and tissue volume 22. It is desirable for temperature sensor 34 to be positioned outside of beam path 16 such that it does not experience heating from directly impinging acoustic energy. For example, in some aspects of the invention, temperature sensor 34 is placed within coolant exhaust port 33, allowing it to measure the highly-relevant temperature of the cooling fluid within heat removal element 20. In other aspects of the invention, two temperature sensors are used, one at the inlet to heat removal element 20 and one at the outlet from heat removal element 20 (e.g., coolant exhaust port 33). The difference between the readings at these two sensors, when combined with the rate at which the cooling fluid flows through heat removal 20, allows calculation of the amount of heat being removed from tissue volume 22.

Temperature readings from temperature sensor 34 may be output and presented as advisory data to a practitioner, for example via a display (e.g., a color, number, or symbol), a tone (e.g., an audible alarm), and/or haptic or vibratory feedback. This allows the practitioner to adjust the rate at which acoustic energy is delivered by transducer 14 and/or the rate at which thermal energy is removed via heat removal element 20 in order to maintain a particular temperature or temperature range at temperature sensor 34. Of course, as discussed in greater detail below, temperature sensor 34 may also allow a feedback control system to provide overtemperature protection (either of transducer 14 or tissue volume 22), for example by triggering an automatic power reduction or cutoff if the temperature exceeds a certain value.

Temperature sensor 34 may also be part of a feedback control system that manipulates the rate at which transducer 14 delivers acoustic energy to tissue volume 22 and/or the rate at which heat removal element 20 removes heat from tissue volume 22. Such manipulation can be used to ensure that thermal necrosis does not occur above dashed line 26. For example, a practitioner may preset the depth above which thermal necrosis is undesirable based upon the likely or known depth of coronary arteries 24, and a controller may control the rate at which transducer 14 delivers acoustic energy into tissue volume 22 and/or the rate at which heat removal element 20 removes thermal energy from tissue volume 22 to maintain a corresponding temperature or temperature range at temperature sensor 34. For example, if the temperature rises beyond a preset threshold temperature at which thermal necrosis is possible in superficial tissues, the controller can reduce the rate at which acoustic energy is delivered (e.g., by reducing the intensity of the acoustic energy emitted by transducer 14) and/or increase the rate at which thermal energy is removed (e.g., by increasing the flow rate of the cooling fluid through chamber 28). Conversely, if the temperature drops below a preset threshold temperature at which successful lesion creation in deeper tissue is compromised, the controller can increase the rate at which acoustic energy is delivered and/or reduce the rate at which thermal energy is removed.

Alternatively, such manipulation may be used to set or adjust the depth of dashed line 26. For example, by increasing the rate at which transducer 14 delivers acoustic energy to tissue volume 22 (e.g., by increasing the power level of transducer 14) and/or by decreasing the rate at which heat removal element 20 removes heat from tissue volume 22 (e.g., by decreasing the cooling fluid flow rate), dashed line 26 may be moved closer to the surface of tissue volume 22. Conversely, by decreasing the rate at which transducer 14 delivers acoustic energy to tissue volume 22 and/or by increasing the rate at which heat removal element 20 removes heat from tissue volume 22, dashed line 26 may be moved deeper into tissue volume 22.

In general, therefore, the relationship between the power level of the transducer 14 and the cooling rate of the heat removal element 20 may be determined (e.g., based on empirical data that relates the depth of line 26 to certain operating parameters) and then exploited (e.g., by manipulating the delivery of acoustic energy to tissue volume 22 and/or the removal of thermal energy from tissue volume 22) in the treatment of atrial fibrillation or ventricular rhythm disorders. As used herein, the term "power level" refers to both the intensity and exposure time of the acoustic energy, while the term "cooling rate" encompasses heat transfer via any mode (e.g., convection, conduction, and radiation).

As mentioned above, one reason it may be desirable to avoid thermal necrosis to a preset depth is to avoid damaging coronary arteries. Accordingly, in some embodiments of the invention, at least one coronary artery detection element is carried on distal end portion 12 of the probe. Suitable coronary artery detection elements include, but are not limited to, infrared detectors, acoustic Doppler sensors, pulsatility sensors, and microphones (e.g., acoustic microphones, sonic microphones, and audio microphones). Detection may also be via any suitable imaging modality (e.g., ultrasound imaging using transducers 14, fluoroscopy). Once such structures have been detected, the feedback control system described above may be programmed such that the preset depth is below the detected structures. Distal end portion 12 of the probe may also carry one or more electrodes usable for pacing, sensing, electrophysiological mapping, localization, and the like. Electrodes in a bipolar configuration should have at least one electrode of a pair in direct contact with tissue, whereas, in a unipolar configuration, the single electrode should contact myocardial tissue. Moreover, it is desirable for the electrodes to have smooth surfaces and adequate surface area for a particular application.

Figure 2:
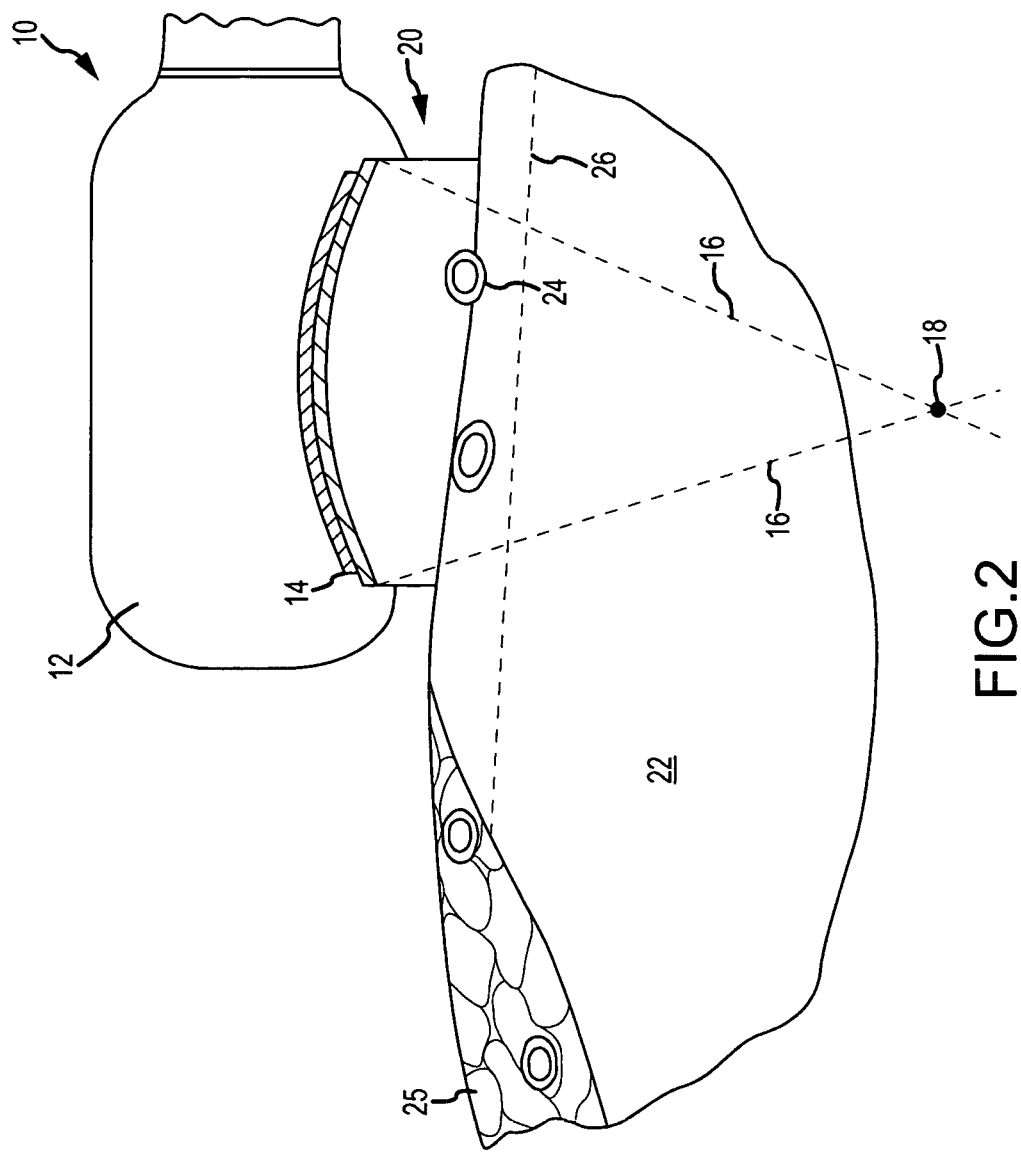
FIG. 2 depicts a tissue ablation system according to another embodiment of the present invention.

FIG. 2 illustrates a second embodiment of tissue ablation system 10 that is substantially similar to the embodiment of FIG. 1. In FIG. 2, however, heat removal element 20 is a heat sink instead of a convective heat removal element. As used herein, the term "heat sink" refers to an element that at least conducts heat, and which may also radiate heat and provide for convective heat transfer (e.g., to surrounding air). Typically, the heat sink will be solid or solid like and be metallic or metal-containing, though the use of non-metallic heat sinks (e.g., chambers filled with gel) is regarded as within the spirit and scope of the present invention. One of ordinary skill in the art will appreciate that the acoustic energy emitted by transducer 14 will "stir" any flowable material within heat removal element 20, even if totally sealed therein; this effect is useful and desirable in isothermalizing heat removal element 20. Moreover, this "stirring" also results in convective heat transfer into heat removal element 20 through the mode of heat transfer sometimes referred to as "natural convection."

Figure 3:
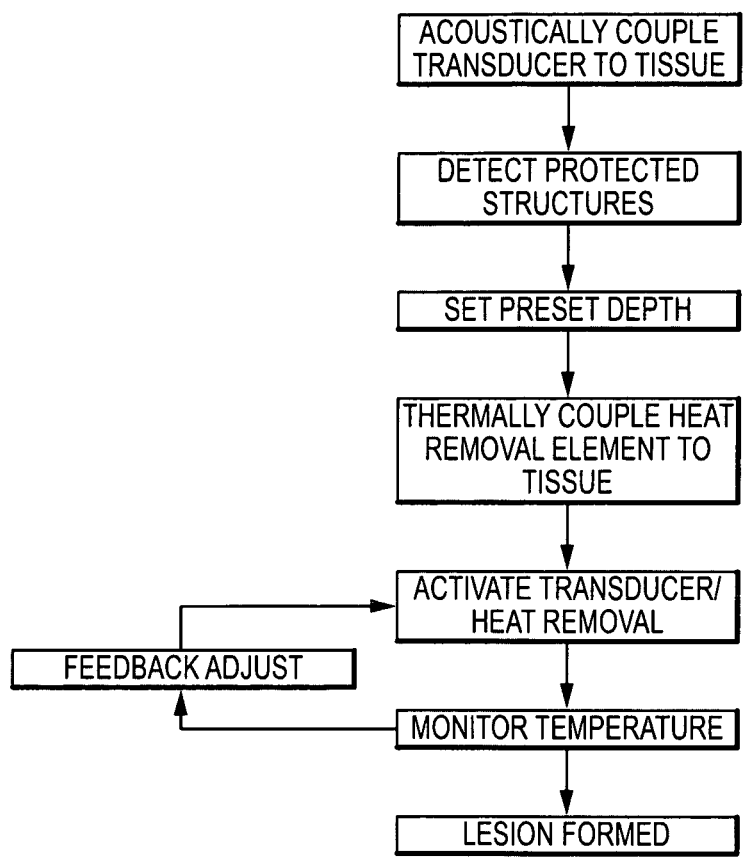
FIG. 3 is a flowchart of steps that may be carried out in practicing a method according to the present invention.

In use, and as illustrated in FIG. 3, transducer 14 is acoustically coupled and heat removal element 20 is thermally coupled to the tissue to be treated. Of course, as discussed above, transducer 14 may be acoustically coupled to the tissue to be treated via heat removal element 20. A detection element may then be utilized to detect any structures that are to be protected from thermal necrosis, and the depth above which thermal necrosis should be avoided may be preset accordingly. Alternatively, or in addition, transducer 14 may be utilized in a Doppler mode to perform acoustic Doppler detection of coronary flow in order to detect the structures to be protected.

Transducer 14 is then activated to deliver acoustic energy to the tissue to be treated. Sufficient thermal energy is removed from the tissue being treated via heat removal element 20 to prevent thermal necrosis to a preset depth in the tissue while simultaneously delivering sufficient acoustic energy into the tissue to be treated to cause thermal necrosis beyond the preset protected depth. This may be accomplished, for example, by controlling the pressure, volume flow rate, and/or temperature of a cooling fluid flowing through heat removal element 20 and/or by manipulating the power level and/or frequency of the acoustic energy delivered by transducer 14. Energy delivery and heat removal may occur simultaneously, sequentially, or in a time-interleaved manner. That is, in some embodiments of the invention, heat removal element 20 operates simultaneously with transducer 14, while in other embodiments of the invention, heat removal element 20 operates in turn with transducer 14. It sill other embodiments of the invention as discussed above, heat removal element 20 operates before transducer 14 to precool tissue volume 22, advantageously allowing for additional power delivery to deeper tissue without overheating more superficial tissue. In addition, lesion formation and/or tissue thickness may be monitored via pulse-echo feedback using transducer 14 if desired.

Although several embodiments of this invention have been described above with a certain degree of particularity, those skilled in the art could make numerous alterations to the disclosed embodiments without departing from the spirit or scope of this invention.

For example, while the present invention has been described in connection with acoustic transducers (e.g., HIFU transducers), it should be understood that the principles herein can be applied equally well to laser ablation elements.

As another example, the heat removal element may be separately introduced into the patient on a second probe rather than carried on the same probe as the transducer or other ablation element.

As a further example, the practitioner may be provided with data, such as typical operating conditions or a chart showing the protected depth for a given set of acoustic energy delivery and thermal energy removal conditions, as an alternative or in addition to the feedback control system described herein.

Still another example contemplates the use of a solid annular ring as the heat removal element. The hole in the middle of the ring may be filled with flowing saline to support transmission of acoustic energy from the transducer to the tissue volume; the walls of the annular ring constrain this flowing cooling fluid to the space between the transducer and the target tissue. To exhaust the cooling fluid, a slot may be provided in the annular ring; a temperature sensor may be provided within the slot. It is also contemplated that a flexible and acoustically transparent membrane may be provided over the open face of the annular ring.

It is also contemplated that, rather than flowing the cooling fluid through the heat removal element, it may be flowed across the heat removal element (e.g., across its outer surface rather than through its interior).

All directional references (e.g., upper, lower, upward, downward, left, right, leftward, rightward, top, bottom, above, below, vertical, horizontal, clockwise, and counterclockwise) are only used for identification purposes to aid the reader's understanding of the present invention, and do not create limitations, particularly as to the position, orientation, or use of the invention. Joinder references (e.g., attached, coupled, connected, and the like) are to be construed broadly and may include intermediate members between a connection of elements and relative movement between elements. As such, joinder references do not necessarily infer that two elements are directly connected and in fixed relation to each other.

It is intended that all matter contained in the above description or shown in the accompanying drawings shall be interpreted as illustrative only and not limiting. Changes in detail or structure may be made without departing from the spirit of the invention as defined in the appended claims.

What is claimed is:
1. A tissue ablation system, comprising:
a probe having a distal end portion;
at least one transducer carried on the distal end portion of the probe and capable of emitting acoustic energy along a beam path;
at least one acoustically transparent heat removal element adapted to be thermally coupled to a tissue volume within the beam path of the at least one transducer, the at least one acoustically transparent heat removal element including a fluid-receiving chamber adapted to receive a cooling fluid therein;

at least one temperature sensor disposed within the fluid-receiving chamber in order to directly monitor a temperature of the cooling fluid therein; and a feedback controller operably coupled to the at least one transducer, in communication with the at least one temperature sensor, and programmed to:

receive a depth parameter defining a superficial layer of the tissue volume to be protected from thermal necrosis;

determine a flow rate of the cooling fluid based on the depth parameter; and operate the at least one transducer to manipulate a rate at which the at least one transducer delivers energy to the tissue volume in response to at least the depth parameter and the temperature of the cooling fluid such that thermal necrosis does not occur in the superficial layer of the tissue volume.

2. The system according to claim 1, wherein the at least one acoustically transparent heat removal element is carried on the distal end portion of the probe and is thermally coupled to the at least one transducer to remove thermal energy from the at least one transducer.

3. The system according to claim 2, wherein the fluid-receiving chamber is at least partially enclosed by a flexible membrane, wherein the flexible membrane permits the at least one transducer to be conformably acoustically coupled to the tissue volume.

4. The system according to claim 1, wherein the at least one acoustically transparent heat removal element further comprises at least one heat sink.

5. The system according to claim 1, wherein the at least one acoustically transparent heat removal element is part of a closed-loop flowed cooling system.

6. The system according to claim 1, wherein the at least one acoustically transparent heat removal element is part of an open-loop flowed cooling system.

7. The system according to claim 6, wherein the at least one acoustically transparent heat removal element includes at least one fluid outlet through which a cooling fluid may be discharged in vivo.

8. The system according to claim 1, wherein the at least one acoustically transparent heat removal element has a thickness and a maximum lateral dimension, and wherein the thickness is less than the maximum lateral direction.

9. The system according to claim 1, further comprising at least one coronary artery detection element carried on the distal end portion of the probe.

10. The system according to claim 9, wherein the feedback controller is in communication with the at least one coronary artery detection element, and is further programmed to determine the depth parameter from an output of the at least one coronary artery detection element.

11. The system according to claim 9, wherein the at least one coronary artery detection element is selected from the group consisting of: infrared detectors, microphones, acoustic Doppler sensors, and pulsatility sensors.

12. The system according to claim 1, further comprising at least one electrode carried on the distal end portion of the probe.

13. The system according to claim 1, wherein the at least one temperature sensor is positioned outside the beam path of the at least one transducer.

14. The system according to claim 13, wherein the at least one temperature sensor is positioned at at least one of a point of entry for the cooling fluid into the at least one acoustically transparent heat removal element and a point of exit for the cooling fluid from the at least one acoustically transparent heat removal element.

15. The system according to claim 1, wherein the feedback controller is further programmed to operate the at least one transducer in order to maintain a target temperature as measured by the at least one temperature sensor, wherein the target temperature is selected such that the superficial layer of the tissue volume remains below a tissue necrosis temperature.

16. The system according to claim 1, wherein the feedback controller is further programmed to vary the flow rate of the cooling fluid.

17. A tissue ablation system, comprising:

a feedback controller programmed to:

receive a depth parameter defining a superficial layer of a tissue volume to be protected from thermal necrosis;

monitor a temperature of a flowing cooling fluid; and manipulate a rate at which at least one probe-mounted transducer capable of emitting acoustic energy along a beam path and into the tissue volume delivers acoustic energy into the tissue volume to maintain the temperature of the flowing cooling fluid at a target temperature such that the superficial layer of the tissue volume remains below a tissue necrosis temperature.

18. A tissue ablation system, comprising:

a probe having a distal end portion;

at least one transducer carried on the distal end portion of the probe and capable of emitting acoustic energy along a beam path;

at least one acoustically transparent heat removal element adapted to be thermally coupled to a tissue volume within the beam path of the at least one transducer, the at least one acoustically transparent heat removal element including a fluid-receiving chamber adapted to receive a cooling fluid therein;

at least one temperature sensor disposed within the fluid-receiving chamber in order to directly monitor a temperature of the cooling fluid therein;

at least one detection element operable to detect blood vessels in the tissue volume; and a feedback controller operably coupled to the at least one transducer and in communication with the at least one temperature sensor and the at least one detection element, the feedback controller programmed to:

receive an output of the at least one detection element and determine therefrom a depth parameter defining a superficial layer of the tissue volume to be protected from thermal necrosis, wherein the superficial layer includes the blood vessels detected by the at least one detection element;

set a flow rate of the cooling fluid based on the depth parameter; and operate the at least one transducer to manipulate a rate at which the at least one transducer delivers energy to the tissue volume to maintain a target temperature of the cooling fluid such that the superficial layer of the tissue volume does not exceed a tissue necrosis temperature.

* * * * *